United States Patent [19]

Göhde

[11] 4,056,324
[45] Nov. 1, 1977

[54] APPARATUS FOR COUNTING AND/OR MEASURING PARTICLES SUSPENDED IN A FLUID MEDIUM

[76] Inventor: Hildegard Göhde, von-Stauffenberg-Str. 40, 4400 Munster, Germany

[21] Appl. No.: 683,340

[22] Filed: May 5, 1976

[30] Foreign Application Priority Data

May 10, 1975   Germany .............................. 2521236

[51] Int. Cl.² ............................................ G01N 21/00
[52] U.S. Cl. ..................................... 356/246; 250/576
[58] Field of Search ................. 356/181, 246; 250/576

[56] References Cited
U.S. PATENT DOCUMENTS

| | | | |
|---|---|---|---|
| 3,720,470 | 3/1973 | Berkhan ........................... | 356/103 X |
| 3,738,759 | 6/1973 | Dittrich et al. ................... | 356/246 X |
| 3,893,766 | 7/1975 | Hogg ................................ | 356/246 X |

Primary Examiner—John K. Corbin
Assistant Examiner—Matthew W. Koren
Attorney, Agent, or Firm—Roylance, Abrams, Berdo & Kaul

[57] ABSTRACT

An apparatus for counting and/or measuring small particles suspended in a fluid medium, is provided with an improved flow cell in which the particle carrying fluid medium is fed into a flow channel through which also a particle free liquid is passed for narrowing and extending the flow of the suspension fluid within the channel which by its configuration including a section of continuously decreasing cross sectional area, allows a more precise measurement and avoids clogging of the suspension fluid inlet the diameter of which is not any longer a critical dimension.

8 Claims, 5 Drawing Figures

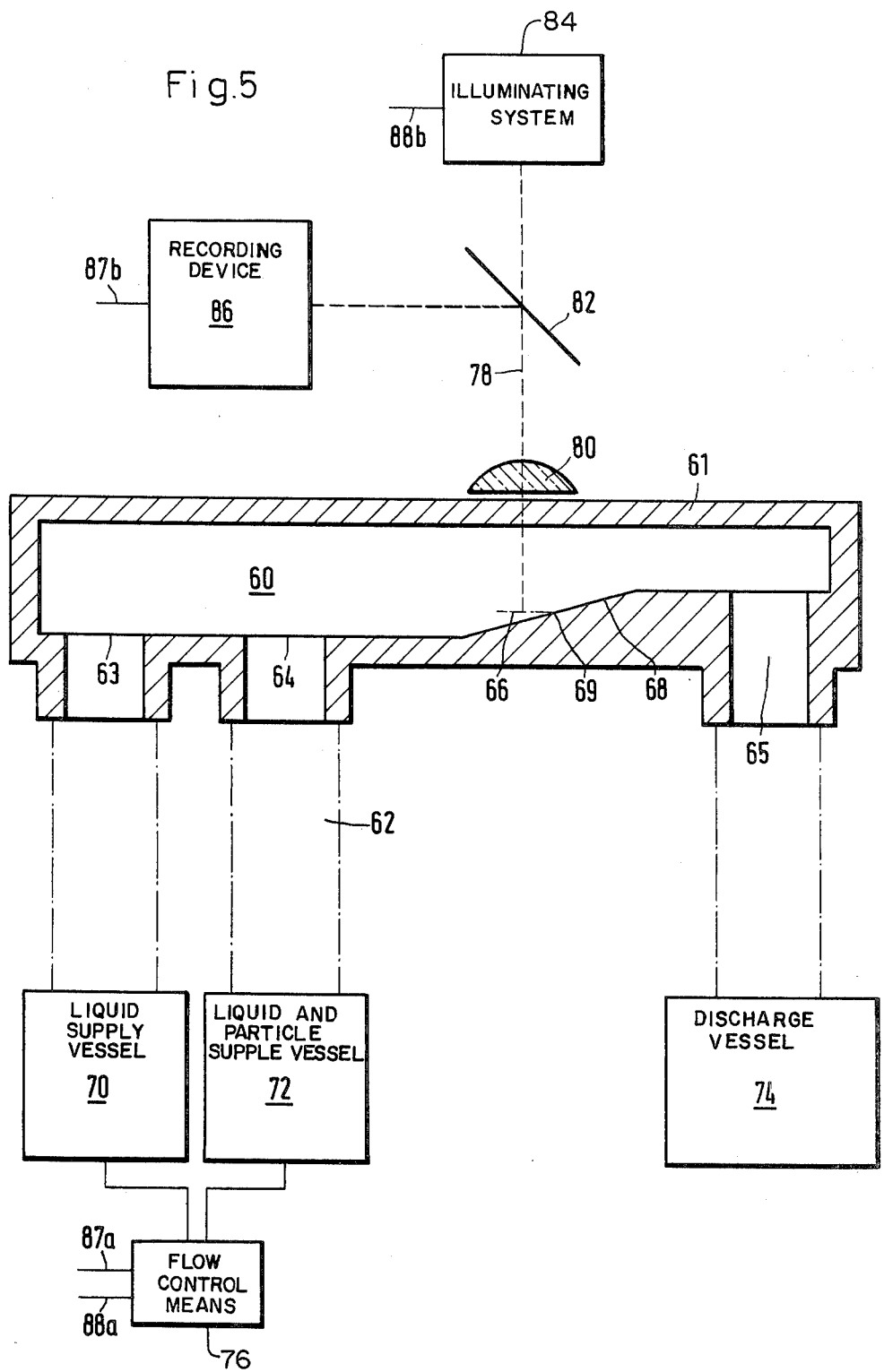

APPARATUS FOR COUNTING AND/OR MEASURING PARTICLES SUSPENDED IN A FLUID MEDIUM

The invention relates to an apparatus for counting and/or measuring particles suspended in a fluid medium, and it is especially concerned with an apparatus of that general type in which a flow cell is provided with a first inlet and an outlet interconnected by a flow channel, and with a second inlet for feeding the suspension into the flow channel through which a liquid is flowing from the first inlet to the outlet. Downstreams of the second inlet, there is an observation area in the channel, the particles being counted or measured when passing through that area.

Apparatuses of that general or a similar type are described in German Pat. No. 2,050,672; they are used in an increasing extent for medical purposes, for instance for the examination of suspensions containing human cells. In U.S. Pat No. 3,738,759, a flow cell is described having a straight flow channel with a first inlet and an outlet at opposite ends, a second inlet forming together therewith a T-like junction. The suspension liquid comprising the cells to be examined, is fed through the second inlet into a stream of a particle free liquid flowing from the first inlet to the outlet. Such device is sometimes called a measuring pore; the observation area which is also the focussing plane of the observation microscope or the object plane, is in this case the interface at which the branch for feeding the suspension opens out into the flow channel for the particle free liquid crossing that branch. That interface should be as small as possible. In practice the diameter is about 0.1 mm or less. Considerable efforts are necessary for manufacturing such flow cells. The measuring conditions, taken alone, are very favourable. However with regard to the small diameter of the measuring pore, there is always the danger that cells collect in the branch near the orifice thereby clogging the measuring pore so that operation of the device is disturbed.

The flow cell described in German Pat. No. 2,050,672 is provided also with a substantially T-like configuration of the flow channel for the particle free liquid and the branch through which the suspension fluid is supplied. However, the observation point is downstreams of that point at which the particle suspension is fed into the channel, the suspension being carried along as a thin layer between the plane bottom and the particle free liquid vehicle which is flowing in parallel to the bottom. Therefore, the field of focus extends in parallel to the bottom of the flow channel and immediately adjacent thereto, but has not only an extension in parallel to the channel bottom but also a non-negligible height because not only those particles are to be recorded which are passing closest to the bottom. In this device it might be possible to make use of a supply inlet for the particle suspension having a larger opening, under condition that the channel clearance is tapering from the mouth of the supply branch of the particle suspension to the measuring point by diminishing the spacing between the side walls and the axis of the channel. The measuring point, however, is in this device in a channel section of uniform clearance. Therefore, also in this type of flow cell described in German Pat. No. 2,050,672, the particles to be examined not only flow along in an interface parallel to the channel bottom but through a three-dimensional area of non-negligible height. For this reason, no precise focussing of the particles during measuring is possible, and on the other hand, the clearance of the supply branch must be kept very small nevertheless. Only in that way, the height of the volume through which the particles are flowing, can be kept as small as possible for obtaining measurements of sufficient precision.

It is a main object of the present invention to provide a flow cell for an apparatus of the above mentioned general type, which cell has a relatively simple configuration and can be manufactured more easily as compared with those cells discussed in detail above.

It is a further object of the invention to provide a flow cell which alows simpler focussing and more precise measurements.

A further object of the invention is to provide a flow cell in which the observation area is practically restricted to a plane interface which is passed by the particles with a velocity component parallel to the optical axis, or axis of observation, and in which nevertheless the branch channel through which the particle suspension is fed into the particle free liquid has an orifice of considerably larger diameter than in the known art.

These and further objects are achieved by a flow cell having a first inlet and an outlet at opposite ends of a flow channel for a liquid vehicle and having a second inlet in the bottom of the channel downstream of the first inlet, and a section of gradually decreasing clearance downstreams of said second inlet, the clearance reduction resulting from an inclination of the substantially plane bottom portion in that section which is also bordered by a plane cover surface forming together with the bottom portion a truncated wedge form. Observations are made through the plane cover surface, and focussing is carried out by "attaching" the field of observation which is a plane interface only, to the inclined bottom so that the particles flowing along the bottom are observed and recorded when passing through the interface. As the particle stream is narrowed when carried along by the vehicular liquid free of particles, the orifice of the supply conduit for the particle suspension may be considerably larger than in known devices of that type. The diameter of the particle stream is at the observation point considerably smaller than at the orifice of the supply branch. As the orifice of the branch can be made larger than formerly, manufacturing is facilitated and the possibility for disturbances which otherwise might occur by clogging of the supply branch, is considerably reduced. That means that there are special advantages in manufacturing as well as in practical use, to be found in the present invention.

Further objects, novel features and advantages of the invention will be apparent from the following description and the drawings in which the features of this invention are shown by way of example.

In the drawings,

FIG. 5 shows schematically an apparatus according to the invention.

Figure 1:
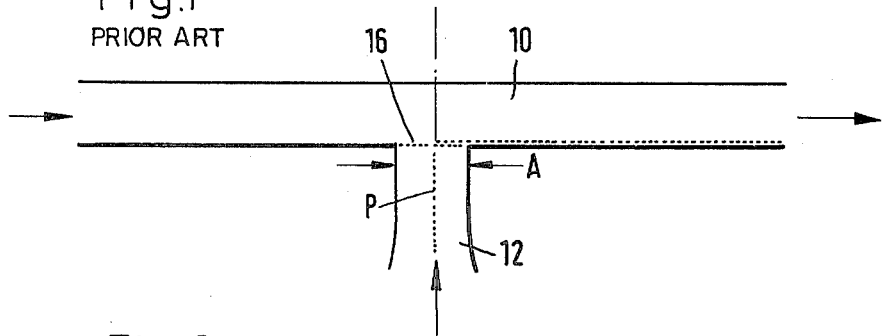
FIGS. 1 and 2 are schematic views of the essential parts of devices described in the above mentioned publications.

A device according to FIG. 1, see also U.S. Pat. No. 3,738,759, comprises a flow channel 10 for a particle free liquid, and a channel 12 for the particle suspension joined thereto in a cross-like form with regard to the axis of channel 10. The cross sectional area of orifice 16 is orientated coaxially to the optical axis 14 and is used as observation area or focussing or object plane, respectively, through which the particles P are flowing. The concentration of the suspension, the flow rate and the diameter A of channel 12 in the measuring area 16 are chosen in that way that the particles are counted and measured individually. The precondition for this is that the diameter A is about 0.1 mm or even less. Apart from the difficulties of manufacturing such device, there is also the risk that the measuring area 16 and/or the channel 12 upstreams thereof, are clogged.

Figure 2:
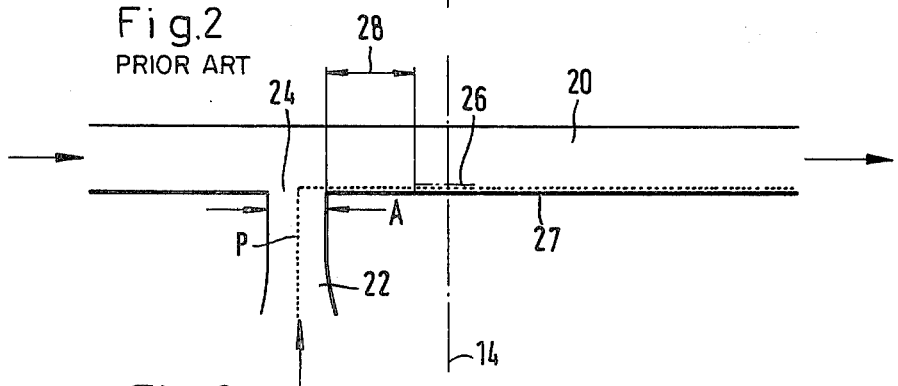

In an apparatus according to FIG. 2, see also German Pat. No. 2,050,672, a supply conduit 22 for the suspension of the particles P which are to be examined, opens by orifice 24 into a flow channel 20 for a particle free liquid vehicle. In this case, the observation area 26 is downstream of orifice 24. The observation area 26 may be spaced by a distance 28 which is shown in FIG. 2 not in the right scale, from orifice 24 so that in the section 28 a tapering of the channel in the direction to the outlet which is in the right part of FIG. 2, may be provided for by decreasing the spacing between the sidewalls of the flow channel 20. Also in this case, flow conditions are adjusted in that way that the particle suspension is passing in a laminar flow in close proximity to the plane bottom 27. But it would be practically impossible to carry along the particles P through the observation area 26 in an exactly plane interface. The particles flow through a volume which extends to a definite height above bottom 27. This, however, excludes a precise focussing of the particles during the measurements. In spite of narrowing the flow of the suspension in which the particles P are dispersed, in the section 28, the diameter A of the orifice area 24 must be kept relatively small, similar to FIG. 1, because otherwise the height of the volume to be observed in the area 26 would be too great.

Figure 3:
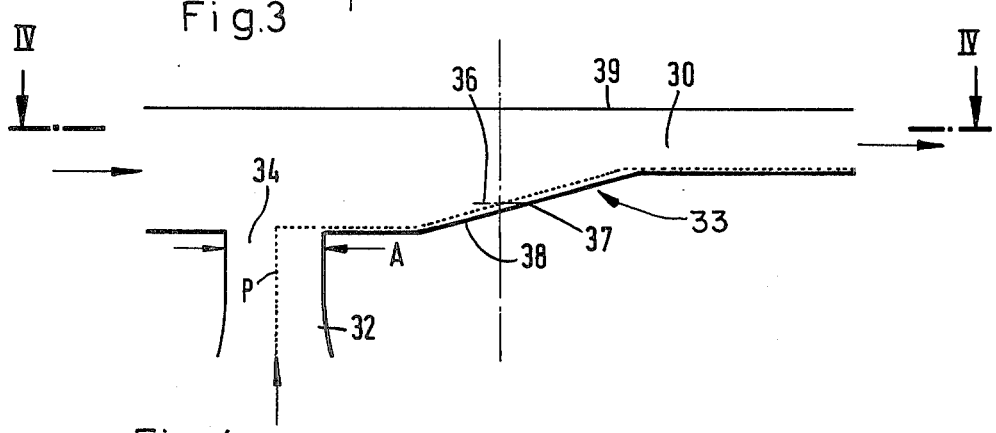
FIG. 3 is a schematic view of the essential parts of a device according to the present invention.
Figure 4:
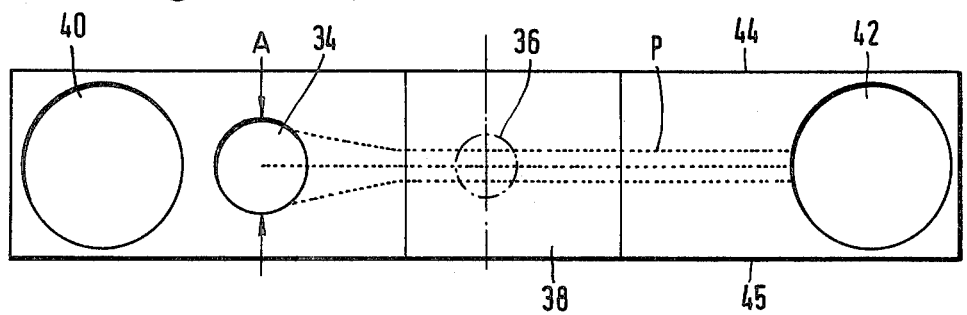
FIG. 4 is a simplified representation of a sectional view along the line IV—IV of FIG. 3

An apparatus according to the present invention, see FIGS. 3 – 5, is provided with a flow cell which is shown in FIGS. 3 and 4, in a simplified manner. In that flow cell, a supply conduit 32 for a suspension in which the particles P are dispersed, opens into a flow channel 30. A liquid vehicle is passed through the flow channel 30, the direction of flow being marked by the arrows shown at the left and at the right end of the channel. The channel 30 is defined by a bottom indicated generally at 33 consisting of plane surface sections, a plane cover 39 and plane parallel sidewalls 44, 45. At the section 38, the bottom is rising in the direction to the outlet 42, thereby the spacing between bottom and cover 39 being reduced in this section continously. Before and behind section 38, the cross sectional area of channel 30 is constant. The apparatus is adjusted in that way that the visual field or object plane 36 forms an interface in parallel to cover 39 in contiguous to the inclined bottom section 38 at 37.

Considering the configuration of the flow cell and the position of visual field 36, the diameter A of the supply channel 32 at the orifice 34 is not as critical as, and may be made considerably wider than, those of the devices shown in FIGS. 1 and 2. The flow rates are adjusted in that way that the liquid vehicle supplied at 40 to the flow channel 34 is washing away the suspension fluid supplied to the channel 30 at 34, in a laminar flow substantially closest to bottom 33, thereby narrowing the flow of the suspension and extending the streamlines in the direction of flow. This effect, also depending on the spacing between orifice 34 and inclined bottom section 38, is amplified by the narrowing of the passage at this section. As the observations are made when the particles are flowing through a plane interface with a velocity component normal thereto, the individual measurements of the particles P are considerably improved over a device according to FIG. 2 in spite of the relatively large cross sectional area at 34 and the simplified adjustment of the microscope.

FIG. 5 shows a complete apparatus according to the invention in a simplified manner. The essential item of this apparatus is a flow cell which according to the invention is made of a transparent material, preferably of glass. In the flow cell a flow channel 60 has a first inlet 63 for the liquid vehicle at its one end, and an outlet 65 at the opposite end. Between both ends, a supply line 62 for a suspension in which the particles to be examined are dispersed, has its orifice at 64. Channel 60 is covered by a plane plate 61, an ocular 80 being mounted immediately above plate 61. The optical axis 78 is adjusted in that way that the object plane 66 of the optical system is parallel to plate 61 and is contiguous to the bottom 68 at 69, the bottom 68 going up in the direction to the outlet at this section.

First inlet 63 and second inlet 62 are connected with liquid supply vessels 70, and 72, respectively, which also comprise liquid conveyor means. These conveyor means are adjusted and controlled by a common control device 76 in that way that in channel 60, a laminar flow is provided and the stream lines of the suspension entering from orifice 64 are narrowed and lengthened downstream thereof, especially in the area of the inclined bottom section 68. A tank or discharge vessel 74 is connected to outlet 65.

By an illuminating system 84, the particles going through the plane of observation 66, are illuminated and will be recorded in the recording device 86 by means of a semi transparent mirror 82. Illuminating device 84 and recording device 86 are connected to control device 76 by conduit means 87a, 87b and 88a, 88b, respectively, so that the apparatus may be operated automatically.

Instead of an observation with illumination from above, the observation and measurements may be carried out also with light going through the channel. For this purpose, a light source or source of radiation is to be mounted accordingly below bottom section 68. When monochromatic light is used, the result of the measurements is not influenced by the prismatic form of the bottom of channel 60 within the section 68. On the other hand, the bottom may be replaced in this part by a plate with parallel faces.

I claim:

1. In an apparatus for counting and/or measuring particles suspended in a fluid medium,
   a flow cell having spaced apart cover wall means and bottom wall means for defining a flow channel therebetween,
   a first inlet to said channel and an outlet from said channel at opposite ends thereof for establishing a general direction of flow in said channel going from said first inlet to said outlet,
   a second inlet to said channel in said bottom means between and spaced from said first inlet and said outlet,
   means in said cover wall means bordering a section of said channel between said second inlet and said outlet defining a window extending substantially parallel with said general direction of flow within said section, said bottom wall means including a substantially plane surface opposite said window and inclined relative to said general direction of flow so that the cross-sectional area of said channel is reduced in said general direction, and observation means having an axis of observation passing through said window for defining an observation area between said window and adjacent said inclined plane surface, said observation area being a plane extending from said inclined plane surface into said channel parallel to said window.

2. A flow cell for the examination of biological cells or small particles suspended in a fluid medium, comprising bottom wall means, sidewall means and cover means defining a substantially straight flow channel, a first inlet and an outlet at opposite ends of said channel, a second inlet to said channel in said bottom wall means between and spaced apart from said first inlet and said outlet, the section of said channel between said second inlet and said outlet being bounded by a plane transparent part of said cover means, two parallel plane parts of said sidewall means, and a plane part of said bottom wall means, said parts defining a channel section having a rectangular cross section, said plane part of said bottom wall means being inclined relative to said plane transparent part so that said rectangular cross section is reduced in the direction toward said outlet.

3. An apparatus for counting and/or measuring small particles suspended in a fluid medium, comprising a source of particle-free liquid, a source of particle-containing suspension liquid, a radiation source, means for detecting and recording radiation, and a flow cell, said flow cell having a bottom wall, sidewalls and a cover defining a flow channel having a first inlet and an outlet at opposite ends thereof, a second inlet in said bottom between and spaced apart from said first inlet and said outlet, means for connecting said first inlet with said source of particle-free liquid, means for connecting said second inlet to said source of suspension liquid, said channel comprising means defining a channel portion between said second inlet and said outlet having a cross-sectional area which gradually decreases in the direction toward said outlet, said section being bordered by a plane transparent window part of said cover and by a part of said bottom inclined relative to said window part, said radiation means and said detecting and recording means having a common axis normal to said window part, said detecting means including optical means defining a detecting area on said axis within said channel in a plane parallel to said window part and contiguous to said inclined portion of said bottom.

4. An apparatus according to claim 3 wherein said inclined portion of said bottom has a plane surface.

5. Apparatus according to claim 3 wherein said sidewalls of said channel are substantially planar and parallel to each other.

6. Apparatus according to claim 3 wherein said second inlet is located in a part of said channel having constant cross sectional area and in which said section of gradually decreasing cross sectional area is spaced apart from said second inlet.

7. Apparatus according to claim 3 wherein said channel portion of gradually decreasing cross sectional area is connected to the outlet by a part of said channel having constant cross sectional area.

8. Apparatus according to claim 3 wherein said inclined portion of said bottom is transparent.

* * * * *